(12) United States Patent
Wang et al.

(10) Patent No.: US 8,884,065 B2
(45) Date of Patent: Nov. 11, 2014

(54) PROCESS FOR PRODUCING CYCLOALKYLAROMATIC COMPOUNDS

(75) Inventors: Kun Wang, Bridgewater, NJ (US); Jihad M. Dakka, Whitehouse Station, NJ (US); Stephen Zushma, Clinton, NJ (US); James R. Lattner, LaPorte, TX (US); Christopher L. Becker, Manhattan, KS (US); Tan-Jen Chen, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/989,903

(22) PCT Filed: Oct. 25, 2011

(86) PCT No.: PCT/US2011/057598
§ 371 (c)(1),
(2), (4) Date: Aug. 16, 2013

(87) PCT Pub. No.: WO2012/082232
PCT Pub. Date: Jun. 21, 2012

(65) Prior Publication Data
US 2014/0187821 A1 Jul. 3, 2014

Related U.S. Application Data

(60) Provisional application No. 61/424,229, filed on Dec. 17, 2010, provisional application No. 61/424,236, filed on Dec. 17, 2010.

(51) Int. Cl.
| | |
|---|---|
| C07C 45/53 | (2006.01) |
| C07C 15/067 | (2006.01) |
| C07C 37/08 | (2006.01) |
| C07C 2/74 | (2006.01) |

(52) U.S. Cl.
CPC ............... *C07C 2/74* (2013.01); *C07C 2529/08* (2013.01); *C07C 45/53* (2013.01); *C07C 2101/14* (2013.01); *C07C 37/08* (2013.01); *C07C 2529/18* (2013.01); *C07C 2529/70* (2013.01)
USPC ............ 568/342; 585/446; 568/569; 568/798

(58) Field of Classification Search
CPC .... C07C 407/00; C07C 2/66; C07C 2529/06; C07C 2529/08; C07C 2529/65; C07C 45/53; C07C 37/08

USPC ............... 568/342, 569, 798; 585/446
See application file for complete search history.

(56) References Cited

U.S. PATENT DOCUMENTS

| | | |
|---|---|---|
| 4,094,918 A | 6/1978 | Murtha et al. |
| 4,122,125 A | 10/1978 | Murtha et al. |
| 4,177,165 A | 12/1979 | Murtha et al. |
| 4,206,082 A | 6/1980 | Murtha et al. |
| 4,219,687 A * | 8/1980 | Dolhyj et al. .................. 502/74 |
| 5,053,571 A | 10/1991 | Makkee |
| 6,037,513 A | 3/2000 | Chang et al. |
| 6,489,529 B1 | 12/2002 | Cheng et al. |
| 6,720,462 B2 * | 4/2004 | Kuhnle et al. ................. 568/768 |
| 6,730,625 B1 | 5/2004 | Chang et al. |
| 6,852,893 B2 | 2/2005 | Kuhnle et al. |
| 7,326,815 B2 | 2/2008 | Dakka et al. |
| 7,446,232 B2 | 11/2008 | Dakka et al. |
| 2002/0169331 A1 | 11/2002 | Miura et al. |
| 2010/0179351 A1 | 7/2010 | Chen et al. |
| 2010/0222609 A1 | 9/2010 | Dakka et al. |
| 2010/0228047 A1 | 9/2010 | Benitez et al. |
| 2010/0234589 A1 | 9/2010 | Dakka et al. |

FOREIGN PATENT DOCUMENTS

| | | |
|---|---|---|
| EP | 1 074 536 | 2/2001 |
| WO | 01/47840 | 7/2001 |
| WO | 2009/128984 | 10/2009 |
| WO | 2010/042273 | 4/2010 |
| WO | 2010/098916 | 9/2010 |
| WO | 2010/138248 | 12/2010 |
| WO | WO2010138248 A2 * | 12/2010 |
| WO | 2011/031374 | 3/2011 |
| WO | 2011/066037 | 6/2011 |
| WO | 2011/100013 | 8/2011 |
| WO | 2012/082232 | 6/2012 |
| WO | 2012/082407 | 6/2012 |

* cited by examiner

*Primary Examiner* — Sikarl Witherspoon
(74) *Attorney, Agent, or Firm* — Jamie L. Sullivan; Siwen Chen (57) ABSTRACT

In a process for producing a cycloalkylaromatic compound, an aromatic compound and a cyclic olefin are contacted with a first catalyst under conditions effective to produce a reaction product comprising the cycloalkylaromatic compound and at least one non-fused bicyclic by-product. The at least one non-fused bicyclic by-product is then contacted with a second catalyst under conditions effective to convert at least a portion of the at least one non-fused bicyclic by-product to a converted by-product.

25 Claims, 3 Drawing Sheets

PROCESS FOR PRODUCING CYCLOALKYLAROMATIC COMPOUNDS

PRIORITY CLAIM

This application is a National Stage Application of International Application No. PCT/US2011/057598 filed Oct. 25, 2011, which claims priority to U.S. Application Ser. No. 61/424,236, filed Dec. 17, 2010; and U.S. Application Ser. No. 61/424,229, filed Dec. 17, 2010, which are incorporated herein by reference in their entirety.

CROSS REFERENCE TO RELATED APPLICATIONS

This application is related to U.S. Publication No. US2010/0234589, published Sep. 16, 2010; U.S. Publication No. US2010/0222609, published Sep. 2, 2010; U.S. Publication No. 2010/0228047, published Sep. 9, 2010; International Patent Cooperation Treaty Publication No. WO2010/042273, published Apr. 15, 2010; International Patent Cooperation Treaty Application No. PCT/US2010/041801, filed Jul. 13, 2010; and International Patent Cooperation Treaty Application No. PCT/US2010/050970, filed Sep. 30, 2010.

FIELD

The present invention relates to a process for producing cycloalkylaromatic compounds and particularly cyclohexylbenzene.

BACKGROUND

Cyclohexylbenzene is a product of increasing importance in the chemical industry since it offers an alternative route to the Hock process for the production of phenol. The Hock process is a three-step process in which benzene is alkylated with propylene to produce cumene, the cumene is oxidized to the corresponding hydroperoxide and then the hydroperoxide is cleaved to produce equimolar amounts of phenol and acetone. However, the world demand for phenol is growing more rapidly than that for acetone. Thus, a process that uses higher alkenes instead of propylene as feed and coproduces higher ketones, rather than acetone, may be an attractive alternative route to the production of phenols.

For example, oxidation of cyclohexylbenzene has a potential as an alternative route for the production of phenol since it co-produces cyclohexanone, which has a growing market and is used as an industrial solvent, as an activator in oxidation reactions and in the production of adipic acid, cyclohexanone resins, cyclohexanone oxime, caprolactam and nylon 6. However, this alternative route requires the development of a commercially viable process for producing the cyclohexylbenzene precursor.

It has been known for many years that cyclohexylbenzene can be produced from benzene either directly by alkylation with cyclohexene or by the process of hydroalkylation or reductive alkylation. In the latter process, benzene is heated with hydrogen in the presence of a catalyst such that the benzene undergoes partial hydrogenation to produce cyclohexene which then alkylates the benzene starting material. Thus, U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffered from the problems that the selectivity to cyclohexylbenzene was low particularly at economically viable benzene conversion rates and that large quantities of unwanted by-products were produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof and the contacting step is conducted at a temperature of about 50 to 350° C., a pressure of about 100 to 7000 kPa, a benzene to hydrogen molar ratio of about 0.01 to 100 and a WHSV of about 0.01 to 100. The '513 patent discloses that the resultant cyclohexylbenzene can then be oxidized to the corresponding hydroperoxide and the peroxide decomposed to the desired phenol and cyclohexanone.

However, although the use of MCM-22 family catalysts has allowed a significant increase in product selectivity, the manufacture of cyclohexylbenzene both by direct alkylation and by benzene hydroalkylation still tends to be accompanied by the co-production of significant amounts of by-products. Some of these by-products, such as cyclohexane and dicyclohexylbenzene, can be readily removed from the cyclohexylbenzene product by distillation. However, certain non-fused bicyclic by-products, such as 1,1-methylcyclopentylbenzene and bicyclohexane, have boiling points too similar to that of cyclohexylbenzene to allow their separation by simple distillation. If not removed, these non-fused bicyclic by-products can build up in, and cause problems with, later stages of the phenol production process. Thus, there is interest in developing processes for removing these non-fused bicyclic by-products from the cyclohexylbenzene product.

According to the invention, it has now been found that non-fused bicyclic by-products in cyclohexylbenzene, and other cycloalkylaromatic products of the alkylation of aromatic compounds with cyclic olefins, can be at least partly removed by treating the non-fused bicyclic by-products with a catalyst, especially an acid catalyst, such as faujasite, either alone or in the presence of benzene.

SUMMARY

In one aspect, the invention resides in a process for producing a cycloalkylaromatic compound, the process comprising:

(a) contacting an aromatic compound and a cyclic olefin with a first catalyst under conditions effective to produce a reaction product comprising the cycloalkylaromatic compound and at least one non-fused bicyclic by-product; and (b) contacting the at least one non-fused bicyclic by-product with a second catalyst under conditions effective to convert at least a portion of the at least one non-fused bicyclic by-product to a converted by-product.

Conveniently, the second catalyst is an acid catalyst, such as an aluminosilicate zeolite, and especially faujasite.

Conveniently, the contacting (b) is conducted at a temperature of about 100° C. to about 350° C. and in one embodiment is conducted in the presence of benzene.

In one embodiment, the aromatic compound is benzene. Conveniently, the cyclic olefin is cyclohexene, the cycloalkylaromatic compound is cyclohexylbenzene and the at least one non-fused bicyclic by-product is selected from 1,1-methylcyclopentylbenzene, bicyclohexane and mixtures thereof.

Conveniently, the effluent from the contacting (a) is separated into at least a $C_6$ fraction comprising unreacted benzene and a $C_{12}$ fraction comprising the cycloalkylaromatic compound and the at least one non-fused bicyclic by-product and the contacting (b) is conducted on the $C_{12}$ fraction.

In a further aspect, the invention resides in a process for producing cyclohexylbenzene, the process comprising:

(a) contacting benzene and hydrogen with a hydroalkylation catalyst under hydroalkylation conditions to produce a reaction product comprising unreacted benzene, cyclohexylbenzene and at least one by-product selected from 1,1-methylcyclopentylbenzene and bicyclohexane; and (b) contacting at least a portion of the reaction product containing the at least one by-product with an acid catalyst under conditions effective to reduce the concentration of the at least one by-product in the reaction product portion.

Conveniently, the hydroalkylation catalyst comprises a metal-containing zeolite of the MCM-22 family.

Conveniently, the process of the further aspect also comprises:

(c) oxidizing the cyclohexylbenzene from the contacting (a) and (b) to produce a cyclohexylbenzene hydroperoxide;

(d) cleaving the cyclohexylbenzene hydroperoxide from the oxidizing (c) to produce phenol and cyclohexanone; and (e) convert at least a portion of the cyclohexanone to phenol.

Conveniently, the process of the further aspect also comprises:

(f) dehydrogenating at least a portion of the cyclohexanone from the cleaving step (e) to produce phenol.

DETAILED DESCRIPTION OF THE EMBODIMENTS

Described herein is a process for producing a cycloalkylaromatic compound by contacting an aromatic compound and a cyclic olefin with a first catalyst under conditions effective to produce the desired cycloalkylaromatic compound and at least one non-fused bicyclic by-product. The present process is particularly intended for producing cyclohexylbenzene for use as a precursor in the production of phenol and cyclohexanone from benzene. The remaining discussion will therefore focus on this particular embodiment, although it is to be appreciated that the present process is equally applicable to the production of other cycloalkylaromatic compounds.

Production of the Cyclohexylbenzene

The hydroalkylation of benzene to produce cyclohexylbenzene proceeds according to the following reaction (1):

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur; and less than 100 ppm, such as less than 30 ppm, for example less than 3 ppm carbon monoxide; and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

The hydroalkylation reaction is effected in the presence of a bifunctional catalyst comprising a molecular sieve and a hydrogenation metal. In one preferred embodiment, the molecular sieve comprises an MCM-22 family material. The term "MCM-22 family material" (or "material of the MCM-22 family" or "molecular sieve of the MCM-22 family"), as used herein, includes molecular sieves made from a building block unit cell, which unit cell has the MWW framework topology. A unit cell is a spatial arrangement of atoms which if tiled in three-dimensional space describes the crystal structure. MWW framework topology is disclosed and described in the "Atlas of Zeolite Framework Types", Fifth Edition, 2001, the entire content of which is incorporated as reference.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); MCM-36 (described in U.S. Pat. No. 5,250,277); MCM-49 (described in U.S. Pat. No. 5,236,575); MCM-56 (described in U.S. Pat. No. 5,362,697);

UZM-8 (described in U.S. Pat. No. 6,756,030); and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is selected from an aluminosilicate, a borosilicate, and a galosilicate the amount of hydrogenation metal present is such that the molar ratio of the aluminum or boron or gallium in the respective molecular sieve to the hydrogenation metal is from about 1.5 to about 1500, for example from about 75 to about 750, such as from about 100 to about 300.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

Although the hydroalkylation reaction using an MCM-22 family zeolite catalyst described herein is highly selective towards cyclohexylbenzene, the effluent from the hydroalkylation reaction may contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

The conditions employed in the hydroalkylation process are important in achieving a lower selectivity for 1,1 MCPB. In one embodiment, the operating conditions and include a temperature of less than 160° C., such as less than 155° C., less than 150° C., less than 145° C. such as from about 125° C. to about 160° C., such as from about 125° C. to about 160° C., such as from about 125° C. to about 150° C., a pressure of about 69 kPag to 2758 kPag (10 psig to 400 psig), particularly about 827 kPag to 1241 kPag (120 psig to 180 psig), and a hydrogen to benzene molar ratio of about 0.01 to about 100. It has been found that reducing the temperature in the hydroalkylation process can be utilized to reduce the formation of 1,1 MCPB in the hydroalkylation process. The temperature reduction can be utilized separately or in combination with the step of contacting the non-fused bicyclic by-product with a catalyst to convert the non-fused bicyclic by-product to a converted by-product as described herein.

Purification of the Cyclohexylbenzene Product

Although the hydroalkylation reaction using an MCM-22 family zeolite catalyst is highly selective towards cyclohexylbenzene (CHB), the effluent from the hydroalkylation reaction will inevitably contain significant quantities of unreacted benzene and certain by-products in addition to the desired cyclohexylbenzene. Generally, the major by-products are cyclohexane (CH), dicyclohexylbenzene (DCHB), methylcyclopentane (MCP), bicyclohexane (BCH), 1,1-methylcyclopentylbenzene (1-MCPB), 1,2-methylcyclopentylbenzene (2-MCPB), and 1,3-methylcyclopentylbenzene (3-MCPB).

1,2-methylcyclopentyl benzene 1,1 methylcyclopentyl benzene 1,3 methylcyclopentyl benzene bicyclohexane 1,1 methylcyclopentyl benzene may also known be known as 1-phenyl-1-methylcyclopentane and (1-methylcyclopentyl)benzene; 1,2 methylcyclopentyl benzene may also be known as 1-phenyl-2-methylcyclopentane and (2-methylcyclopentyl)benzene; 1,3 methylcyclopentyl benzene may also be known as 1-phenyl-3-methylcyclopentane and (3-methylcyclopentyl)benzene; and bicyclohexane may also be known as bicyclohexyl.

A multi-stage distillation process is therefore used to divide the hydroalkylation reaction product into (i) a $C_6$-rich stream comprising cyclohexane and unreacted benzene; (ii) a cyclohexylbenzene-rich $C_{12}$ stream; and (iii) a heavies stream rich in dicyclohexylbenzene. Owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluent.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 500 psig (100 to 3550 kPa), a weight hourly space velocity of about 0.2 to 50 $hr^{-1}$, and a hydrogen to hydrocarbon feed molar ratio of about 0 to about 20.

Owing to the similarity in their boiling points, it is difficult to separate the desired cyclohexylbenzene from non-fused bicyclic by-products such as the bicyclohexane (BCH) and the methylcyclopentylbenzene (MCPB) isomers in the $C_{12}$ stream. Moreover, although 2-MCPB and 3-MCPB are readily converted in the subsequent oxidation/cleavage steps to the phenol and methylcyclopentanones, which are valuable products, 1-MCPB is substantially inert to the oxidation step and so, if not removed will build up in the $C_{12}$ stream. Similarly, BCH can lead to separation problems downstream. Thus, in the present process at least part of the hydroalkylation reaction product is treated with a purification catalyst in a purification zone (e.g., purification reactor) under conditions to remove or reduce at least a portion of at least one non-fused bicyclic by-product such as 1-MCPB and/or BCH from the product. In a preferred embodiment, the at least one non-fused bicyclic by-product is contacted with the purification catalyst prior to the cleavage step. In a more preferred embodiment, the at least one non-fused bicyclic by-product is contacted with the purification catalyst prior to the oxidation step. In one embodiment, the alkylation catalyst and the purification catalyst are different.

In one embodiment, the reaction product comprises at least 0.01 wt % of the non-fused bicyclic by-products, at least 0.02 wt % of at least one of the non-fused bicyclic by-products, at least 0.03 wt % of at least one of the non-fused bicyclic by-products, at least 0.04 wt % of at least one of the non-fused bicyclic by-products, at least 0.05 wt % of at least one of the non-fused bicyclic by-products, at least 0.06 wt % of at least one of the non-fused bicyclic by-products, at least 0.07 wt % of at least one of the non-fused bicyclic by-products, at least 0.08 wt % of at least one of the non-fused bicyclic by-products, at least 0.09 wt % of at least one of the non-fused bicyclic by-products, at least 0.1 wt % of at least one of the non-fused bicyclic by-products.

Although the amount of at least one non-fused cyclic by-product is not narrowly defined, generally the at least one non-fused cyclic by-product is contacted with the purification catalyst is contacted with the purification catalyst in an amount such that the weight ratio of the at least one non-fused cyclic by-product to the cycloalkylaromatic compound as measured at the input to the purification zone is in the range of from 1:1000 to 1000:1; for example in the range of from 1:500 to 500:1, in the range of from 1:100 to 100:1, in the range of from 1:250 to 1:1, and in the range of from 1:100 to 1:1.

In one embodiment, the conversion of the non-fused bicyclic compound after treatment of the purification catalyst is greater than 10 wt %, greater than 20 wt %, greater than 30 wt %, greater than 40 wt %, greater than 50 wt %, greater than 60 wt %, greater than 70 wt %, greater than 80 wt %, and greater than 90 wt %.

In one embodiment, the hydrogen being supplied to the alkylation step comprises at least 10 wt % of the aromatic compound. In another embodiment, the hydrogen being supplied to the alkylation step comprises at least 25 wt % of the aromatic compound. In one embodiment, the hydrogen being supplied to the alkylation step comprises at least 50 wt % of the aromatic compound.

In other embodiments, the weight ratio of the at least one non-fused cyclic by-product to the cycloalkylaromatic compound lower limit may be 1:1000, 1:900, 1:800, 1:700, 1:600, 1:500, 1:400, 1:300; 1:200 and 1:100 and the upper limit weight ratio of the at least one non-fused cyclic by-product to the cycloalkylaromatic compound may be 0.001:1, 0.1:1, 0.5:1:1, 1:1, 100:1, and 1000:1 with ranges from any lower limit to any upper limit being contemplated.

The purification catalyst is generally an acid catalyst, such as an aluminosilicate zeolite, and especially faujasite (e.g., zeolite X, zeolite Y, zeolite USY) and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1-MCPB to the more readily oxidizable 2-MCPB and 3-MCPB. The bicyclohexane is believed to react with benzene present in the hydroalkylation reaction product to produce cyclohexane and additional cyclohexylbenzene according to the following reaction:

An acid catalyst is generally a catalyst having an alpha value of greater than one. In one embodiment, the purification catalyst has an alpha value of greater than one, greater than 2, greater than 5, greater than 10, greater than 15, greater than 20, greater than 25, greater than 30, greater than 35, greater than 40, greater than 45, and greater than 50. In this respect, the alpha value is an approximate indication of the catalytic cracking activity of a material as compared to a standard catalyst. It gives the relative rate constant of the material for hexane cracking (rate of normal hexane conversion per volume of catalyst per unit time) compared to the activity of a standard silica-alumina cracking catalyst taken as an Alpha of 1 (Rate Constant=0.016 sec$^{-1}$). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395 (1980).

In one embodiment, the purification catalyst has a BET surface area greater than 500 m$^2$/g, typically greater than 600 m$^2$/g and a pore volume greater than 0.5 cc/g, typically greater than 0.7 cc/g.

As will be discussed in more detail below, the catalytic treatment can be conducted on the direct product of the hydroalkylation reaction or after distillation of the hydroalkylation reaction product to separate the C$_6$ and/or the heavies fraction.

Depending on the amount of dicyclohexylbenzene present in the heavies stream (iii), it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, including large pore molecular sieves such as a molecular sieve of the MCM-22 family, zeolite beta, MCM-68 (see U.S. Pat. No. 6,014,018), zeolite Y, zeolite USY, and mordenite. A large pore molecular sieve has an average pore size in excess of 7 Å in some embodiments or from 7 Å to 12 Å in other embodiments. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 hr$^{-1}$ on total feed, and a benzene/dicyclohexylbenzene weight ratio about of 1:1 to about 5:1. The transalkylation reaction effluent can then be returned to the second distillation tower to recover the additional monocyclohexylbenzene product produced in the transalkylation reaction. Average pore size can be obtained by nitrogen gas adsorption-desorption analysis.

The cyclohexylbenzene-rich stream separated from the hydroalkylation reaction product is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N''-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N''-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide can be optionally diluted in an organic solvent inert to the cleavage reaction, such as methyl ethyl ketone, cyclohexanone, phenol or cyclohexylbenzene, to assist in heat removal. The cleavage reaction can be conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

Figure 1:
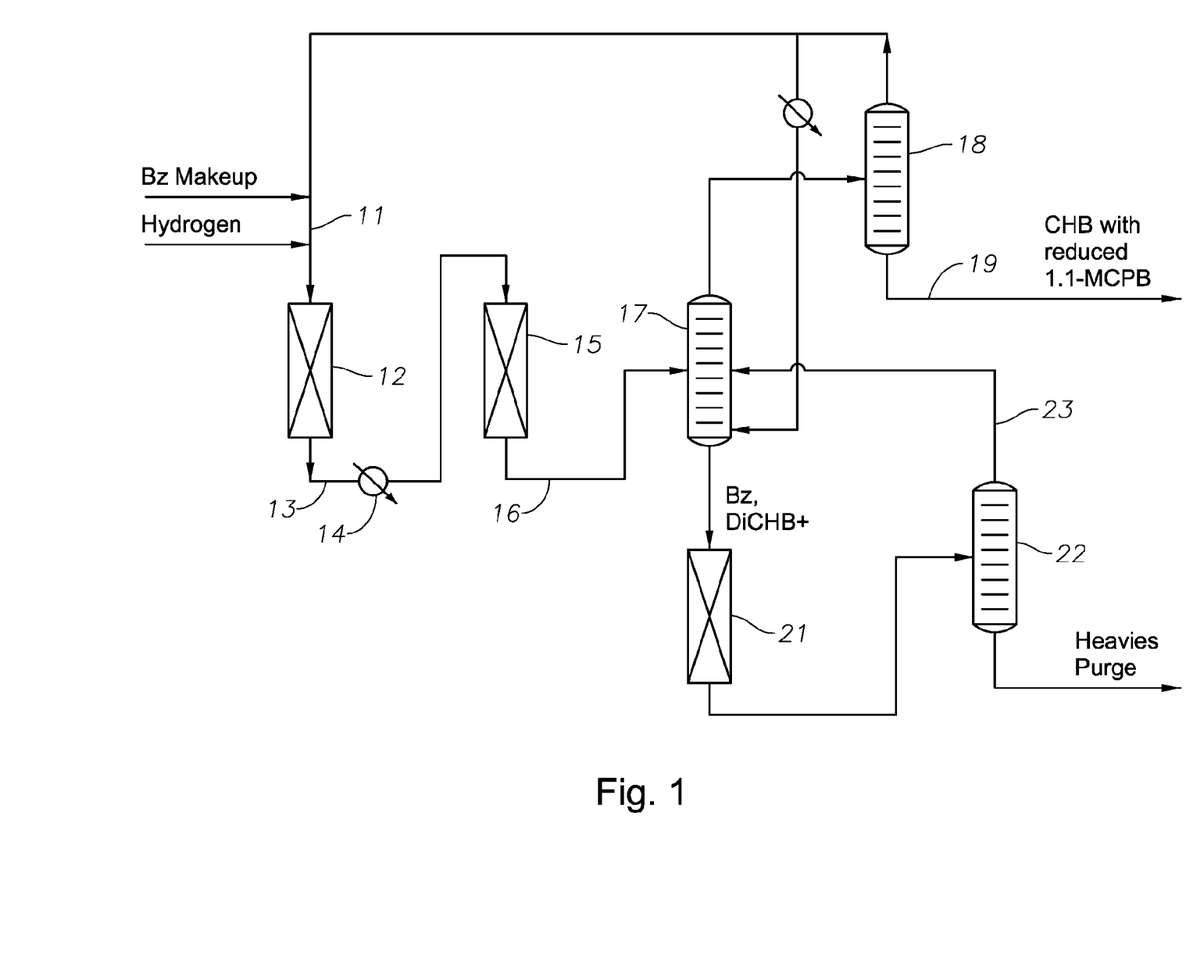
FIG. 1 is a flow diagram of a benzene hydroalkylation process according to a first example of the invention in which the entire hydroalkylation reaction effluent is treated with a faujasite catalyst prior to separation of the effluent into a $C_6$-rich stream, a cyclohexylbenzene-rich stream and a heavies stream.

Referring now the drawings, FIG. 1 illustrates a benzene hydroalkylation process according to a first example of the invention in which make-up benzene and hydrogen are combined and fed via line 11 to a hydroalkylation unit 12. The benzene and hydrogen react in the hydroalkylation unit 12 to produce cyclohexylbenzene (CHB) and certain by-products including cyclohexane (CH), dicyclohexylbenzene (DCHB), methylcyclopentane (MCP), bicyclohexane (BCH), 1,1-methylcyclopentylbenzene (1-MCPB), 1,2-methylcyclopentylbenzene (2-MCPB), and 1,3-methylcyclopentylbenzene (3-MCPB).

The effluent from the hydroalkylation unit 12 is fed by line 13 to a heater 14 and then to a reactor 15, which contains faujasite and which at least partly removes bicyclohexane (BCH) and 1,1-methylcyclopentylbenzene (1-MCPB) in the hydroalkylation effluent. The product from the reactor 15 is then fed via line 16 to a first distillation tower 17, which removes dicyclohexylbenzene (DCHB) and other heavies from the product as a bottoms stream. The overhead from the first distillation tower 17 is then passed to a second distillation tower 18 which divides the overhead into a cyclohexylbenzene-rich $C_{12}$ stream and a $C_6$-rich stream comprising cyclohexane and unreacted benzene. The $C_{12}$ stream is recovered in line 19 for passage to the oxidation and cleavage sections of the process, whereas the $C_6$-rich stream is recycled partly to the hydroalkylation unit 12 and partly to the bottoms stream from the distillation tower 17.

The bottoms stream from the first distillation tower 17, together with unreacted benzene recycled from the second distillation tower 18, are then passed to a transalkylation unit 21 where the dicyclohexylbenzene (DCHB) in the bottoms stream is converted to cyclohexylbenzene (CHB). The effluent from the transalkylation unit 21 is then fed to a third distillation tower 22, where the cyclohexylbenzene (CHB) and unreacted benzene are removed and returned by line 23 to the first distillation tower 17. The bottoms from the third distillation tower 22 is purged or used as fuel.

Figure 2:
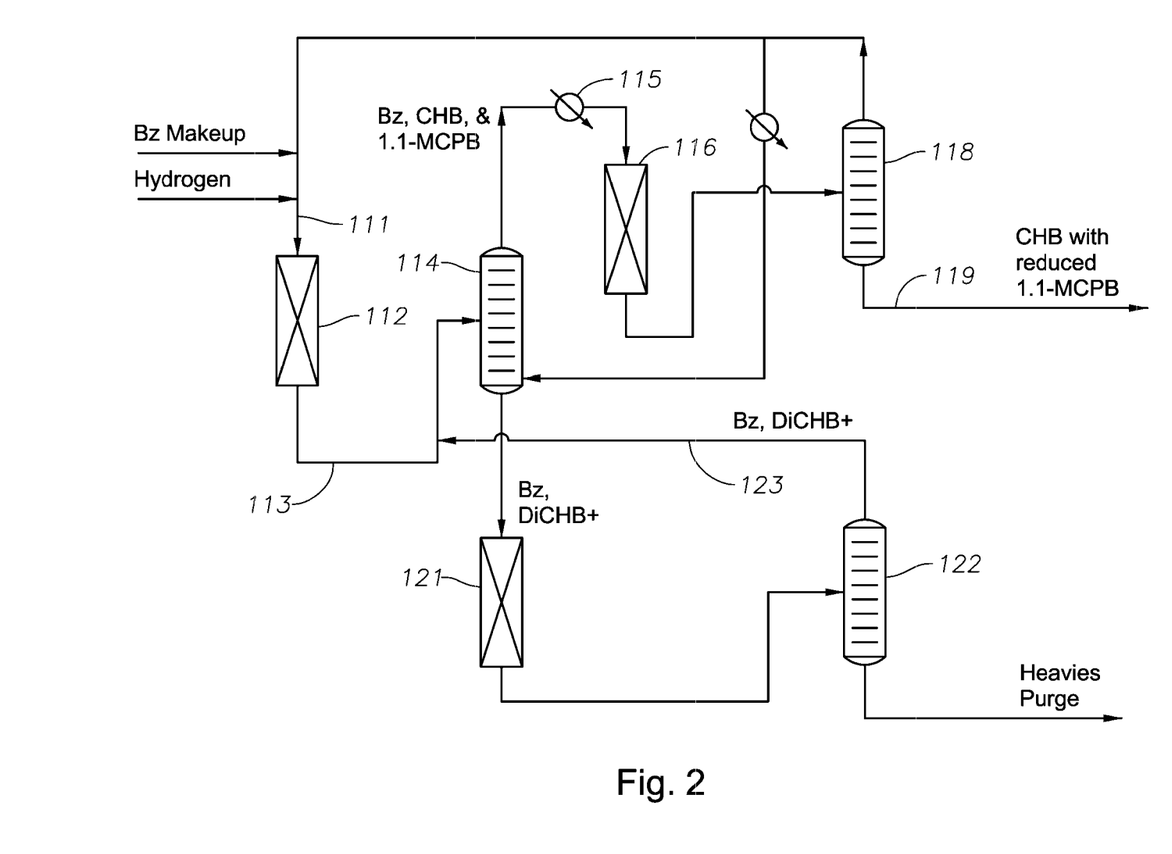
FIG. 2 is a flow diagram of a benzene hydroalkylation process according to a second example of the invention in which a heavies stream is separated from the hydroalkylation reaction effluent before the remainder of the effluent is treated with a faujasite catalyst.

A benzene hydroalkylation process according to a second example of the invention is shown in FIG. 2 in which a hydroalkylation unit 112 receives a combined hydrogen and benzene feed through line 111. The effluent from the hydroalkylation unit 112 is fed by line 113 to a first distillation tower 114, which removes dicyclohexylbenzene (DCHB) and other $C_{18}$+ heavies from the effluent as a bottoms stream. The $C_{18}$- overhead from the first distillation tower 114 is then passed via a heater 115 to a faujasite-containing reactor 116, which at least partly removes bicyclohexane (BCH) and 1,1-methylcyclopentylbenzene (1-MCPB) from the $C_{18}$- fraction.

The reaction product from the reactor 116 is then fed to a second distillation tower 118, which divides the product into a cyclohexylbenzene-rich $C_{12}$ stream and a $C_6$-rich stream comprising cyclohexane and unreacted benzene. The $C_{12}$ stream is recovered in line 119 for passage to the oxidation and cleavage sections of the process, whereas the $C_6$-rich stream is recycled partly to the hydroalkylation unit 112 and partly to the bottoms stream from the distillation tower 114.

The bottoms stream from the first distillation tower 114, together with unreacted benzene recycled from the second distillation tower 118, are then passed to a transalkylation unit 121 where the dicyclohexylbenzene (DCHB) in the bottoms stream is converted to cyclohexylbenzene (CHB). The effluent from the transalkylation unit 121 is then fed to a third distillation tower 122, where the cyclohexylbenzene (CHB) and unreacted benzene are removed and returned by line 123 to the first distillation tower 114. The bottoms from the third distillation tower 122 is purged or used as fuel.

Figure 3:
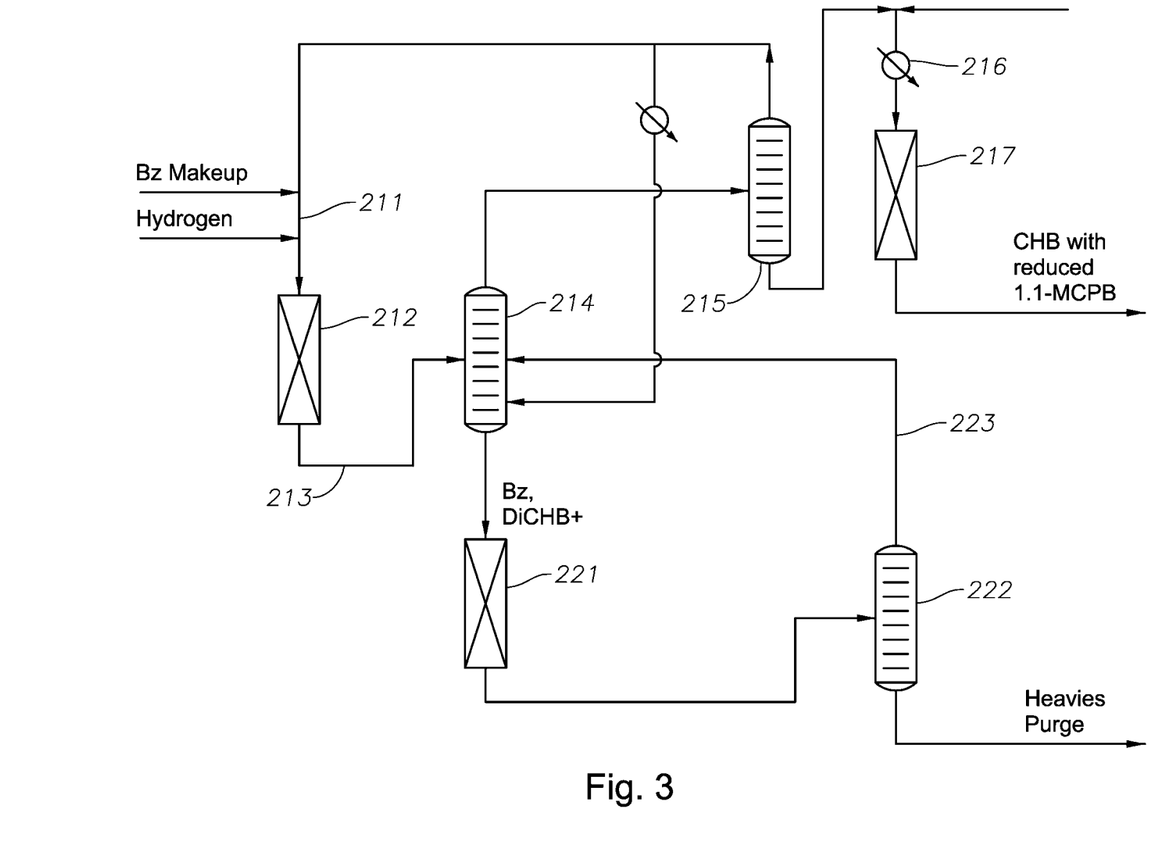
FIG. 3 is a flow diagram of a benzene hydroalkylation process according to a third example of the invention in which a heavies stream and a $C_6$-rich stream are separated from the hydroalkylation reaction effluent before the cyclohexylbenzene-rich product stream is treated with a faujasite catalyst.

A benzene hydroalkylation process according to a third example of the invention is shown in FIG. 3 in which a hydroalkylation unit 212 receives a combined hydrogen and benzene feed through line 211. The effluent from the hydroalkylation unit 212 is fed by line 213 to a first distillation tower 214, which removes dicyclohexylbenzene (DCHB) and other heavies from the effluent as a bottoms stream. The overhead from the first distillation tower 214 is then passed to a second distillation tower 215, which divides the overhead into a cyclohexylbenzene-rich $C_{12}$ stream and a $C_6$-rich stream comprising cyclohexane and unreacted benzene.

The cyclohexylbenzene-rich $C_{12}$ stream from the second distillation tower 215 is then passed via a heater 216 to a faujasite-containing reactor 217, which can also receive recycled cyclohexylbenzene from downsream processing steps. The faujasite in the reactor 217 at least partly removes bicyclohexane (BCH) and 1,1-methylcyclopentylbenzene (1-MCPB) in the cyclohexylbenzene-rich $C_{12}$ stream so that, after passage through the reactor the stream can be fed to the oxidation and cleavage sections of the process.

The bottoms stream from the first distillation tower 214, together with unreacted benzene recycled from the second distillation tower 215, are then passed to a transalkylation unit 221 where the dicyclohexylbenzene (DCHB) in the bottoms stream is converted to cyclohexylbenzene (CHB). The effluent from the transalkylation unit 221 is then fed to a third distillation tower 222, where the cyclohexylbenzene (CHB) and unreacted benzene are removed and returned by line 223 to the first distillation tower 214. The bottoms from the third distillation tower 222 is purged or used as fuel.

The invention will now be more particularly described with reference to the following non-limiting Examples.

The zeolite USY used in the following examples is an ultrastable version of zeolite Y both of which are faujasites having a silica to alumina ratio of approximately 60; unit cell size of approximately 24 Angstroms, total BET surface area (m2/g) of approximately 650, a zeolite surface area of approximately 550, a pore volume of approximately 0.75, and a alpha value of approximately 45.

EXAMPLE 1

Hydroalkylation Catalyst Preparation (0.24 wt % Pd/MCM-49/$Al_2O_3$)

The catalyst in this example was produced by first preparing a Pd on $Al_2O_3$ hydrogenation catalyst. The palladium precursor used was palladium nitrate. The alumina support used was Catalox Hta-101 from Sasol. The catalyst was prepared by impregnating the alumina support with a solution of the palladium precursor and then dried in air at 120° C. The dried Pd alumina was then calcined in air at 350° C. for 3 hours. The palladium concentration on alumina was 0.6 wt %.

The resultant hydrogenation catalyst was then mixed thoroughly with MCM-49 acidic zeolite and Versal 300 pseudoboehmite which had been jet milled to 2 microns in average particle size. The weight ratio of the three components was 0.4 hydrogenation catalyst:0.4 MCM-49:0.2 Versal 300.

A 2 wt % HNO3/water solution was then added to the mixture above to form a thick paste with a solids content 65 wt %. The mixture was then forced through a press with a die plate to form 1/20" (0.13 cm) extrudate. The extrudate was then calcined at 538° C. in air before it was tested for its performance in hydroalkylation.

EXAMPLE 2

CHB Production Via Benzene Hydroalkylation

The catalyst of Example 1 was tested in the hydroalkylation of benzene to produce cyclohexylbenzene (CHB) at two different temperatures, 145° C. and 164° C. Weight hourly space velocity was kept constant at 1.75 $hr^{-1}$ and the hydrogen/benzene molar ratio of the feed was kept constant at 0.65. Reactor pressure was 150 psig (1135 kPa). The results are summarized in Table 1.

TABLE 1

| Temperature, ° C. | 145 | 164 |
|---|---|---|
| Conversion, wt % | 35.5 | 54.2 |
| MCP Selectivity, % | 0.07 | 0.17 |
| CH Selectivity, % | 8.69 | 7.73 |
| CHB Selectivity, % | 75.5 | 68.3 |
| DCHB Selectivity, % | 12.2 | 18.3 |
| 2-MCPB Selectivity, % | 0.39 | 0.68 |
| 1-MCPB Selectivity, % | 0.06 | 0.17 |
| 3-MCPB Selectivity, % | 0.84 | 1.00 |

As can be seen from Table 1 above, conversion was 54.2 wt % at 164° C. reactor temperature and dropped to 35.5 wt % when the reactor temperature was decreased to 145° C.

In benzene hydroalkylation, some of the undesired by-products include cyclohexane (CH), dicyclohexylbenzene (DCHB), methylcyclopentane (MCP), 1,1-methylcyclopentylbenzene (1-MCPB), 1,2-methylcyclopentylbenzene (2-MCPB), and 1,3-methylcyclopentylbenzene (3-MCPB). As can be seen from Table 1, selectivity to cyclohexane actually increased to 8.69 wt % from 7.73 wt % when reaction temperature was decreased. The selectivity to 3-MCPB was not significantly affected by reaction temperature.

An unexpected result of the above tests is that the formation of 1-MCPB can be controlled by reactor temperature. The selectivity to 1-MCPB can be reduced by over 50% by decreasing reaction temperature by 19° C.

EXAMPLE 3

CHB Production Via Transalkyation of DCHB

In this Example, the transalkylation of dicyclohexylbenzene with benzene over various zeolite catalysts, namely mordenite, MCM-22, and Zeolite USY, was investigated.

In each case, one gram of the zeolite catalyst in the 20 to 40 mesh size range was diluted with sand to a volume of 3 cc and charged to a fixed-bed reactor with ⅜ inch (0.95 cm) outside diameter. The catalyst was dried in the reactor with 100 cc/min flowing $N_2$ at 125° C. at 1 atmosphere pressure for 2 hours. The nitrogen supply was then turned off and the reactor pressure increased to 300 psig (2170 kPa). A feed containing 75 wt % benzene and 25 wt % p-dicyclohexylbenzene (DCHB) by weight was introduced to the reactor via an ISCO pump at 60 cc/h for one hour while the reactor was heated to desired temperature. The feed rate was reduced to 4.5 cc/h (WHSV=4) and the test was commenced. Liquid products were collected in a chilled trap and analyzed by GC off-line. The results are summarized in Table 2.

TABLE 2

| Catalyst | Mordenite | MCM-22 | Zeolite USY |
|---|---|---|---|
| Binder | 35% alumina | 20% alumina | |
| Days on stream | 1.8 | 2.8 | 24 |
| Temperature (° C.) | 180 | 180 | 180 |
| DCHB conversion (%) | 79.3 | 16.0 | 81.1 |
| Selectivity (wt %) | | | |
| Lights | 9.21 | | |
| Methylcyclopentane | 0.151 | 0.26 | 0.794 |
| Cyclohexane | 0.746 | 0.2 | |
| Toluene | | | |
| Methylcyclopentylbenzene | 22.45 | 3.85 | 1.34 |

TABLE 2-continued

| Catalyst | Mordenite | MCM-22 | Zeolite USY |
|---|---|---|---|
| (MCPB) | | | |
| 1,1-MCPB/total MCPB | 0.17 | 0.25 | 0.04 |
| Other $C_{12}$ | 1.51 | 3.38 | 0.57 |
| CHB | 69.95 | 62.92 | 96.42 |
| Other $C_{18}$ | 5.097 | 18.9 | 0.84 |

It will be seen from Table 2 that with the Zeolite USY, the formation of 1,1-MCPB was significantly reduced in the transalkylation reaction, with the 1,1-MCPB concentration in the $C_{12}$ fraction being about 500 ppm, as compared to 3.8 wt % for the mordenite catalyst and 1 wt % for MCM-22 catalyst.

EXAMPLE 4

Destruction of 1,1-MCPB in Hydroalkylation Products Diluted with Benzene Over Zeolite USY A mixture of products from benzene hydroalkylation was diluted with an equal weight of benzene. The mixture was then fed through a fixed bed reactor packed with one gram of alumina bound high silica/alumina molar ratio zeolite USY (80 wt % USY, 20 wt % alumina) at a temperature of 170° C., a liquid pressure of 300 psig (2170 kPa), and a space velocity (WHSV) of 4/hour. The composition of feed and product are shown in Table 3 below.

EXAMPLE 5

Destruction of 1,1-MCPB in the Hydroalkylation Products Over Fauiasite Catalyst

A mixture of products from benzene hydroalkylation (without benzene diluent) was fed through a fixed bed reactor packed with one gram of alumina bound high silica/alumina molar ratio zeolite USY (80 wt % USY, 20 wt % alumina) at a temperature of 170° C., a liquid pressure of 300 psig (2170 kPa), and a space velocity (WHSV) of 4/hour. The composition of feed and product are shown in Table 3.

TABLE 3

| Wt % Distr. | Example 4 | | Example 5 | |
|---|---|---|---|---|
| Component | Feed | Product | Feed | Product |
| MCP | 0.019 | 0.063 | 0.024 | 0.088 |
| Benzene | 82.115 | 81.194 | 74.576 | 75.442 |
| CyH | 1.636 | 1.817 | 2.467 | 2.488 |
| Cy= | | | 0.010 | |
| 1,2-MCPB-1 | 0.091 | 0.149 | 0.123 | 0.151 |
| 1,1-MCPB | 0.137 | 0.011 | 0.141 | 0.018 |
| 1,3-MCPB | 0.122 | 0.204 | 0.125 | 0.172 |
| 1,2-MCPB-2 | 0.029 | 0.037 | 0.026 | 0.029 |
| PhCpMethane | 0.006 | 0.011 | 0.007 | 0.014 |
| Ph—MCP = −1 | | 0.022 | | 0.021 |
| CHB | 12.914 | 15.103 | 19.951 | 19.940 |
| Ph—MCP = −2 | | 0.049 | | 0.060 |
| 1-Ph-1-Cy = | | | | |
| diPhCy-1 | 0.030 | 0.029 | 0.018 | 0.028 |
| C18H26-1 | 0.029 | | 0.033 | |
| C18H26-2 | 0.029 | 0.009 | 0.028 | 0.009 |
| o-DCHB | 0.050 | 0.008 | 0.061 | 0.007 |
| diPhCy-2 | 0.000 | 0.004 | | 0.004 |
| C18H26-3 | 0.043 | 0.021 | 0.020 | |
| C18H26-4 | 0.022 | 0.007 | | |
| C18H26-5 | 0.016 | | | 0.004 |
| MCP-Cy-Bz | 0.041 | | 0.038 | |
| m-DCHB | 0.902 | 0.676 | 0.646 | 0.787 |
| diPhCy-3 | | | | |

TABLE 3-continued

| Wt % Distr. | Example 4 | | Example 5 | |
|---|---|---|---|---|
| Component | Feed | Product | Feed | Product |
| diPhCy-4 | 0.030 | 0.041 | 0.041 | 0.042 |
| diPhCy-5 | | | | |
| diPhCy-6 | | 0.015 | | 0.012 |
| p-DCHB | 1.466 | 0.281 | 1.346 | 0.450 |
| UID C18-1 | 0.046 | 0.015 | 0.035 | 0.014 |
| UID C18-2 | 0.042 | 0.020 | 0.046 | 0.019 |
| UID C18-3 | 0.098 | 0.095 | 0.113 | 0.100 |
| UID C18-4 | | 0.020 | | 0.019 |
| UID C18-5 | 0.041 | 0.055 | 0.081 | 0.039 |
| UID C24?-1 | 0.017 | 0.014 | 0.018 | 0.015 |
| UID C24?-2 | 0.031 | 0.029 | 0.027 | 0.027 |

It will be seen from Table 3 that the zeolite USY treatment was effective in reducing the concentration of 1,1-MCPB in the hydroalkylation product both with and without the addition of a benzene diluent.

EXAMPLE 6

Conversion of Bicyclohexane (BCH) Using Faujasite

A mixture of benzene and bicyclohexane (Aldrich) in the weight ratio of 6/1 was fed through a fixed bed reactor packed with 1.0 g of faujasite catalyst (80% faujasite, 20% alumina) at temperature of 170 to 250° C., a liquid pressure of 300 psig (2170 kPa), and a space velocity (WHSV) of 4/h. The liquid products were collected in a pot, which was sampled and analyzed by GC. A mass balance of 100±2% was observed through each run. The composition of feed and product are shown in the Table 4 below. Clearly BCH can be significantly converted when treated with zeolite USY in this manner.

TABLE 4

| Temperature (°C.) | Feed | 170 | 200 | 250 |
|---|---|---|---|---|
| Area % by GC | | | | |
| Cyclohexane | 0.003 | 0.003 | 0.004 | 0.106 |
| Benzene | 90.869 | 90.940 | 91.435 | 94.906 |
| Bicyclohexane | 9.077 | 8.897 | 8.506 | 4.311 |
| Cyclohexylbenzene | 0.000 | 0.139 | 0.021 | 0.059 |
| BCH conv. (wt %) | | 1.983 | 6.291 | 52.506 |
| CHB sel (wt %) | | 97.89 | 84.00 | 35.76 |
| CH sel (wt %) | | 2.11 | 16.00 | 64.24 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing a cycloalkylaromatic compound, the process comprising:
   (a) contacting an aromatic compound and a cyclic olefin with a first catalyst under conditions effective to produce a reaction product comprising the cycloalkylaromatic compound and at least one non-fused bicyclic by-product; and
   (b) contacting at least a portion of the at least one non-fused bicyclic by-product and at least a portion of the cycloalkylaromatic compound with a second catalyst under conditions effective to convert at least a portion of the at least one non-fused bicyclic by-product to a converted by-product, and wherein the second catalyst is an acid catalyst.

2. The process of claim 1, wherein the feed to contacting step (b) comprises a weight ratio of the non-fused bicyclic by-product to the cycloalkylaromatic compound of from 1:1000 to 1000:1 as measured at the input to the contacting step (b).

3. The process of claim 1, wherein the contacting step (b) converts at least 50 wt % of the at least one non-fused bicyclic by-product to a converted by-product.

4. The process of claim 1, wherein the reaction product comprises at least 0.01 wt % of the at least one non-fused bicyclic by-product.

5. The process of claim 1, wherein the first catalyst and the second catalyst are different.

6. The process of claim 1, wherein at least 10 wt % of the aromatic compound is supplied to contacting step (a) based on total amount of hydrocarbon supplied to the contacting step (a).

7. The process of claim 1, wherein the second catalyst comprises an aluminosilicate zeolite.

8. The process of claim 1, wherein the second catalyst comprises faujasite.

9. The process of claim 1, wherein the contacting step (b) is conducted at a temperature of about 100° C. to about 350° C.

10. The process of claim 1, wherein the contacting step (b) is conducted in the presence of benzene.

11. The process of claim 1, wherein the contacting step (b) is conducted on at least a portion of the entire reaction product of the contacting step (a) without separation of the reaction product.

12. The process of claim 1, wherein the contacting step (b) is conducted on a portion the reaction product of the contacting step (a) remaining after separation of a fraction boiling above and/or below the boiling point of the cycloalkylaromatic compound.

13. The process of claim 1, wherein the aromatic compound is benzene.

14. The process of claim 13, wherein the cyclic olefin is cyclohexene and the cycloalkylaromatic compound is cyclohexylbenzene.

15. The process of claim 14, wherein the contacting step (a) is conducted in the presence of hydrogen and cyclohexene is produced by hydrogenation of benzene during the contacting step (a).

16. The process of claim 15, wherein the first catalyst comprises a metal-containing zeolite of the MCM-22 family.

17. The process of claim 1, wherein the at least one non-fused bicyclic by-product is selected from 1,1-methylcyclopentylbenzene, bicyclohexane and mixtures thereof.

18. The process of claim 1, wherein the at least one non-fused bicyclic by-product is 1,1-methylcyclopentylbenzene.

19. The process of claim 1, wherein the at least one non-fused bicyclic by-product is bicyclohexane.

20. The process of claim 14, and further comprising:
   (c) oxidizing at least a portion of the cyclohexylbenzene from the contacting step (a) to produce a cyclohexylbenzene hydroperoxide; and
   (d) cleaving at least a portion of the cyclohexylbenzene hydroperoxide from the oxidizing (c) to produce phenol and cyclohexanone.

21. The process of claim 14, wherein the contacting step (b) is conducted on at least a portion of the entire reaction product of the contacting step (a) without separation of the reaction product.

22. The process of claim 14, wherein the contacting step (b) is conducted on a portion the reaction product of the contacting step (a) remaining after separation of a heavies fraction comprising dicyclohexylbenzene.

23. The process of claim 14, wherein the contacting step (b) is conducted on a portion the reaction product of the contacting step (a) remaining after separation of a $C_6$ fraction comprising unreacted benzene.

24. The process of claim 14, wherein the contacting step (b) is conducted on a $C_{12}$ fraction of the reaction product of the contacting step (a) comprising cyclohexylbenzene and at least one by-product.

25. The process of claim 14, wherein the contacting step (a) is conducted at a temperature of less than 160° C. to reduce the formation of 1,1-methylcyclopentylbenzene in contacting step (a).

* * * * *